United States Patent [19]

Chester et al.

[11] Patent Number: 4,515,168

[45] Date of Patent: May 7, 1985

[54] CLAMP-ON NERVE STIMULATOR AND LOCATOR

[76] Inventors: Martin H. Chester, 25310 Tierra Grande Dr., Carmel, Calif. 93921; Cary A. Norman, 440 Juniper Ave., Pacific Grove, Calif. 93950

[21] Appl. No.: 516,213

[22] Filed: Jul. 22, 1983

[51] Int. Cl.³ .................... A61H 39/02; A61N 1/32
[52] U.S. Cl. .................... 128/741; 128/784; 128/421
[58] Field of Search .............. 128/784, 303.18, 303.14, 128/419 P, 419 PG, 741, 642, 329 A, 419 R, 907, 303.13, 303.19, 639, 421–423, 783; 604/21; 433/32

[56] References Cited

U.S. PATENT DOCUMENTS

| | | | |
|---|---|---|---|
| 3,078,850 | 2/1963 | Schein et al. | 128/784 |
| 3,682,162 | 8/1972 | Colyer | 128/741 |
| 4,269,174 | 5/1981 | Adair | 128/303.18 |
| 4,279,256 | 7/1981 | Bulalo | 128/784 |
| 4,301,802 | 11/1981 | Poler | 128/303.14 |

Primary Examiner—Lee S. Cohen
Assistant Examiner—Steven Falk
Attorney, Agent, or Firm—Sughrue, Mion, Zinn, Macpeak and Seas

[57] ABSTRACT

A completely self-contained nerve stimulator/locator unit to be clamped on the syringe of a conventional syringe and injection needle assembly. The unit contains a power supply, a pulse generating circuit, a patient detector switch for automatically activating the generator when the injection needle touches the patient's body, a manually controlled current-adjusting potentiometer for permitting the physician to adjust the current values of the pulses, and an indicator for visually indicating the generation of each pulse. An LED/LCD digital display is also provided on the unit for displaying the current values of the pulses applied to the patient's body.

9 Claims, 7 Drawing Figures

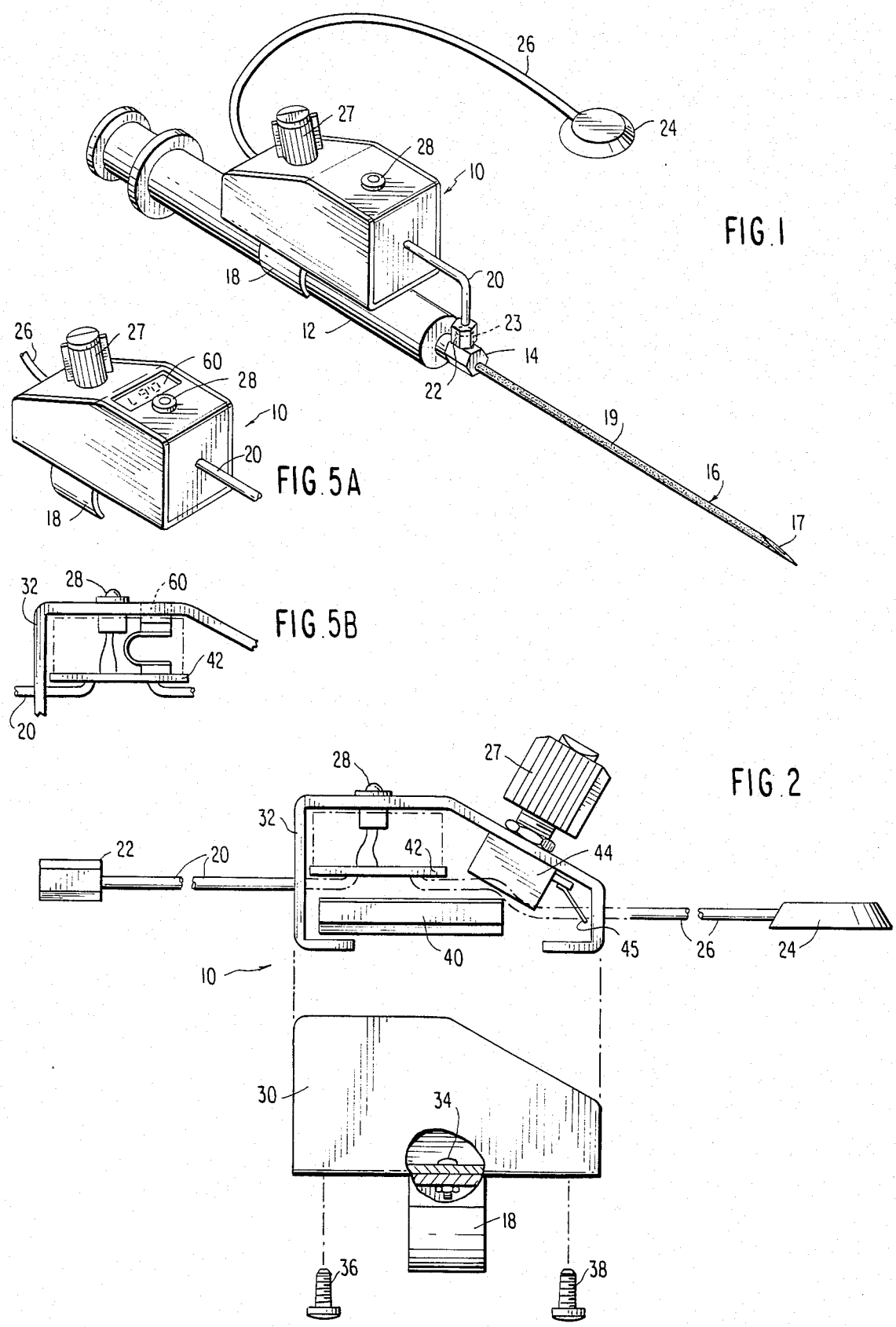

CLAMP-ON NERVE STIMULATOR AND LOCATOR

BACKGROUND OF THE INVENTION

1. Field of the Invention

This invention relates to the field of nerve stimulators and locators of the type which apply an electric current to a nerve in order to obtain a response which locaties the nerve for a physician prior to the injection of an anesthetic or neurolytic agent for the purpose of blocking the nerve and, more particularly, to such a device which can be clamped onto, and completely supported by, a conventional syringe.

2. Description of the Prior Art

It is common practice for an anesthesiologist to attach a nerve stimulator to either an insulated an uninsulated injection needle during the performance of regional anesthesia. When the tip of the needle approaches the nerve, a pulsed electrical current discharge will depolarize the motor or sensory nerve and cause a twitch of the inervated muscles, or paresthesias should a sensory nerve be involved. By using this technique, the anesthesiologist can use a minimum amount of local anesthetic solution to obtain a satisfactory nerve blockade. A detailed description of this technique appears in Raj et al, "Use of the Nerve Stimulator for Peripheral Blocks", Regional Anesthesia, April-June 1980, pages 14–21. Even though the stimulator device is electrically connected to the injection needle, the stimulator device, itself, is separate from the injection needle and requires operation by an assistant who must be in verbal contact with the physician who is inserting the needle for the purpose of stimulating and locating the nerve and then, subsequently, blocking the nerve by injecting an anesthetic solution.

Similarly, U.S. Pat. No. 3,682,162 discloses the combination of an hypodermic needle and a nerve stimulator, but again this stimulator is separate from the hypodermic needle and requires operation by someone other than the physician who is injecting the needle; furthermore, the needle has a special electrode construction.

U.S. Pat. No. 3,078,850 discloses an electrochemotherapeutic cardiac device in which an electric pulse source is electrically connected to an injection needle, but, again, the pulse source is separated from the needle and must be operated by an assistant while the physician is using the needle.

U.S. Pat. No. 3,830,226 discloses an electrically powered nerve stimulator, but it is not intended to be used in physical combination with a syringe and injection needle.

U.S. Pat. No. 4,164,214 discloses an electrical probe for stimulating the nerve in the dental pulp of teeth, but it is not used in combination with an injection needle.

SUMMARY OF THE INVENTION

Therefore, the broad object of this invention is to provide an improved self-contained nerve stimulator/-locator which can, in its entirety, be clamped onto a conventional syringe which is connected to an injection needle so that the physician, himself, can control the electric current flowing through the needle at the same time he is exploring for a nerve and injecting the patient, whereby an assistant is not required.

Another object of the invention is to provide such an improved nerve stimulator/locator including a visual indication of the flow of an electrical pulse through the injection needle into the patient.

A further object of the invention is to provide such an improved nerve stimulator which is automatically electrically energized when the needle touches a patient's skin.

Still another object of the invention is to provide such an improved clamp-on nerve stimulator/locator which contains means for digitally reading out the amount of current or voltage being applied to the patient, thereby eliminating the requirement for the physician to turn his head to look at a remote indicator panel.

Thus, the various features of the invention include a self-contained nerve stimulator-locator which is entirely clamped on, and supported by, a conventional syringe. The voltage/current control is thus readily accessible to the physician using the syringe. A visual indicator permits the physician easily to monitor the operation of the stimulator. Furthermore, a digital readout may be provided on the stimulator/locator to provide an indication of the electric current/voltage which is being applied to the patient. Also, the improved nerve stimulator/locator contains electronics which automatically apply electric power to the stimulator when the injection needle to which the stimulator is connected touches the patient's skin.

BRIEF DESCRIPTION OF THE DRAWING

FIG. 1 is an overall perspective view showing the improved nerve stimulator/locator clamped on a conventional syringe which is coupled to an injection needle.

FIG. 2 is a side elevational view, partly exploded, of the improved nerve stimulator/locator illustrated in FIG. 1.

FIG. 5A and 5B are fragmentary views of portions of FIGS. 1 and 2, respectively, and illustrate a second embodiment of the invention wherein a digital display is incorporated in the nerve stimulator/locator.

DETAILED DESCRIPTION OF THE PREFERRED EMBODIMENTS

Figure 3:
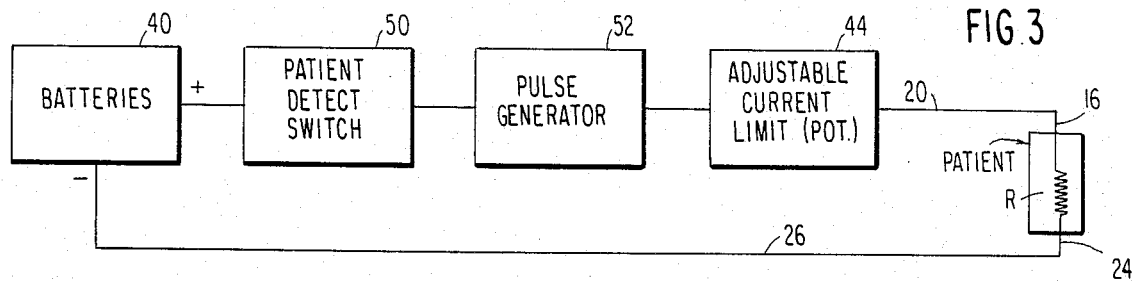
FIG. 3 is a functional block diagram of the electronics embodied in the nerve stimulator/locator illustrated in FIGS. 1 and 2.

FIG. 1 illustrates a preferred embodiment of the invention wherein improved nerve stimulator/locator unit 10 is clamped to, and supported by, a conventional syringe 12 which is connected to the metal hub 14 of an injection needle 16. The stimulator 10 is clamped to the syringe 12 by means of a spring clip 18 which is fixed to the bottom of the stimulator housing. Electrical pulses from the stimulator are applied via an external lead 20 and a connector 22 to the metal hub 14 of the needle 16. The connector 22 at the end of lead 20 clamps onto a metal pin or post 23 integral with the hub 14 and also forming the electrical connection between unit 10 and needle 16. All but the tip 17 of the needle is coated with a non-conducting coating 19 which may be any suitably inert and non-toxic material, such as the materials listed in U.S. Pat. No. 3,078,850. Of course, the needle may be uninsulated as pointed out by Raj et al, but the insulation limits the current flow to the tip of the needle and prevents nerve or direct muscle stimulation by the shaft of the needle. Also, instead of the connector 22, a simple alligator clip may be used to connect the lead 20 to the metal of either the hub 14 or the needle 16.

The circuit through the patient's body is completed by means of an EKG pad 24 which is connected to another external lead 26. The stimulator is effectively connected to the patient by placing the EKG pad on the patient's body at a position remote from the needle but such that the electron flow is concentrated through the area of the nerve which is to be stimulated, located and eventually blocked by injection of an anesthetic or neurolytic solution contained in the syringe and injected through the needle.

A knurled knob 27 on the top of the stimulator 10 is for the purpose of manually controlling an internal potentiometer which regulates the amount of voltage or current applied through the needle. The housing may contain calibration marks roughly to indicate various currents or voltages corresponding to different positions of the knob. An indicator lamp 28, such as an LED, is also positioned on the top of the unit 10 to provide to the physician a visual indication each time a pulse is applied to the patient.

FIG. 2 illustrates the structural details of the stimulator unit illustrated in FIG. 1. The corresponding parts in the two figures carry the same reference numerals. Structurally, the stimulator consists of housing including a base member 30 into which fits a cover member 32. Clip 18 is secured to the base member 30 by means of a suitable fastening means, such as the bolt and nut 34. The cover 32 is secured within the base 30 by means of other suitable fastening means, such as the screws 36 and 38.

Mounted within the cover member 32 is a battery pack 40 and a printed circuit board assembly 42 which contains the electronics for detecting contact of the needle with the patient's skin and for producing the electric pulses which are applied to the needle. The control knob 27 is part of a potentiometer 44 which is secured to the top of the cover 32 and which is electrically connected to lead 26 by a terminal 45.

FIG. 3 is a functional block diagram of the electronics of the stimulator. One terminal of the battery pack 40 is connected through a patient detect switch 50, a pulse generator 52 and the potentiometer 44 to the needle 16. The resistance of the patient's body is represented by the symbol R. The other terminal of the battery pack 40 is connected via the lead 26 and to the EKG pad positioned in electrical contact with the patient's body at a point remote from the needle. Pulses are not generated unless the patient detect switch 50 has detected contact between the needle and the patient's body. The magnitude of the pulses applied to the patient may be manually adjusted by the physician, himself, by his operation of the potentiometer 44.

Figure 4:
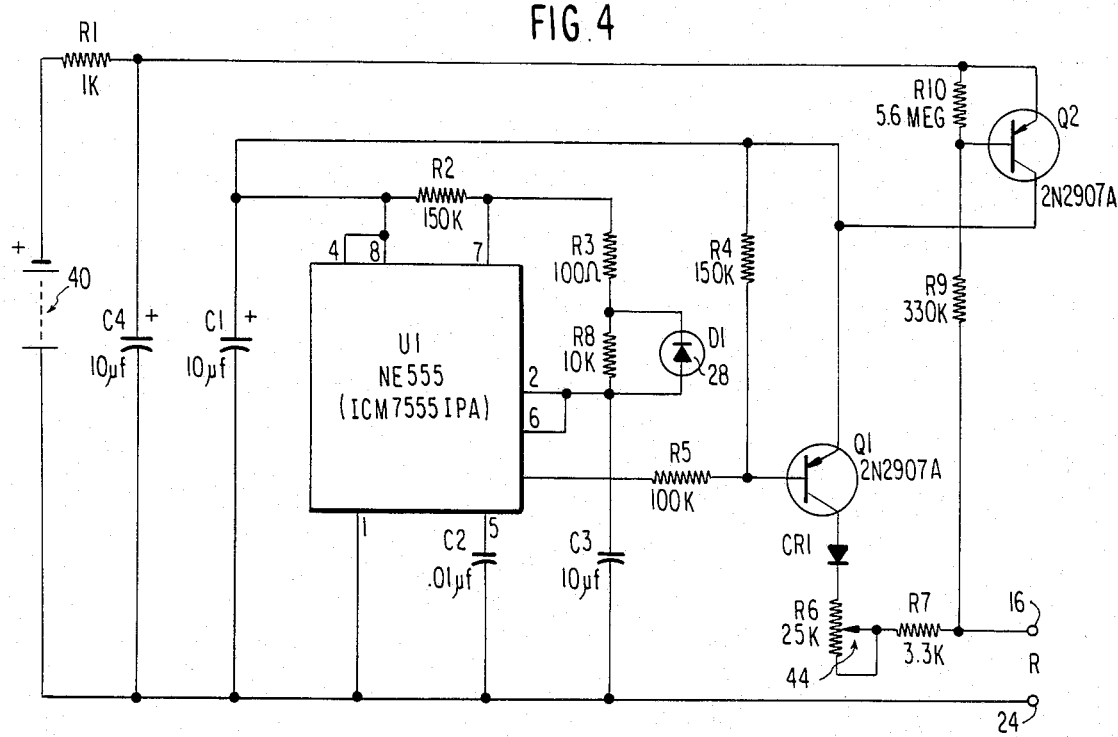
FIG. 4 is a schematic circuit diagram of the electronics illustrated in FIG. 3.

FIG. 4 is a schematic circuit diagram of the electronics illustrated in functional block diagram form in FIG. 3.

The nerve stimulator 10 is designed to generate every second a one millisecond pulse at the maximum voltage of ten volts. The battery pack 40 consists of four 3-volt lithium batteries which have a shelf life of five years. The capacity of the battery pack is rated at 30 milliamp-hours.

Resistor R1 and capacitor C4 form a RC filter network having a time constant of 10 milliseconds. This filter is used to reduce the pulsed current requirement of the circuit so as to produce a constant low current drain on the batteries (when in operation) instead of a higher-current pulsed demand. The integrated circuit U1 is a free-running oscillator with a 0.1% duty cycle. The oscillator timing is provided by the RC network formed by R2, R3, R8 and C3.

The pulse width is determined by diode D1, R3 and C3. The pulse discharge path is through the light-emitting diode (LED) D1 which emits a flash of light at each pulse discharge; thus, minimum energy is required since the timing energy, which would have been wasted, is used to light the LED. During the charging time interval, the diode D1 is effectively out of the circuit since it is back biased in this interval. During discharge, diode D1 is biased in the forward direction, thereby shunting resistor R8. Resistors R5 and R4 provide the base drive for the pulse output drive transistor Q1.

The patient detect switch 50 is formed by the transistor Q2 and the resistors R10 and R9 and is used to detect the completion of a current path between the needle and ground i.e. the EKG pad. This current path is completed when the needle is inserted into the patient's body. A minute current flows from the battery through resistors R10 and R9 and through the patient'body back to the battery. The current is limited by the high value (330K) of resistor R9. When this current flows, transistor Q2 is turned on and supplies operating voltage to the oscillator U1 and for the pulse output transistor Q1. To prevent transisitor Q2 from being erroneously turned on by the collector-to-base Zener action of transistor Q1, a diode CR1 in the collector of transistor Q1 is back biased, thereby preventing transistor Q2 from being turned on in the absence of a completed circuit path. The potentiometer 44 consists of a wiper arm and a 25K resistor R6. A current limiting resistor R7 has a value of 3.3K and limits the current into the patient to a maximum of 3 milliamps. Thus, with the 10 volt battery potential, the potentiometer 44 can be adjusted to provide current pulses in the range of 0.3 milliamps to 3 milliamps.

Thus, once the needle is inserted into the patient, current pulses are automaticaly generated at the rate of one pulse per second. Furthermore, the generation of each pulse is indicated to the physician by the flashing of the light emitting diode D1. Furthermore, the operating physician himself can adjust the potentiometer 44 by manually operating its control knob 27. Since the control knob 27 and light emitting diode 28 are integral with the nerve stimultor/locator unit 10 itself which, in turn, is mounted in its entirety on the syringe 12, there is no requirement for an assistant to operate the stimulator, and the physician need not turn his eyes to obtain an indication of the fact that pulses are being transmitted to the patient's body.

Figure 6:
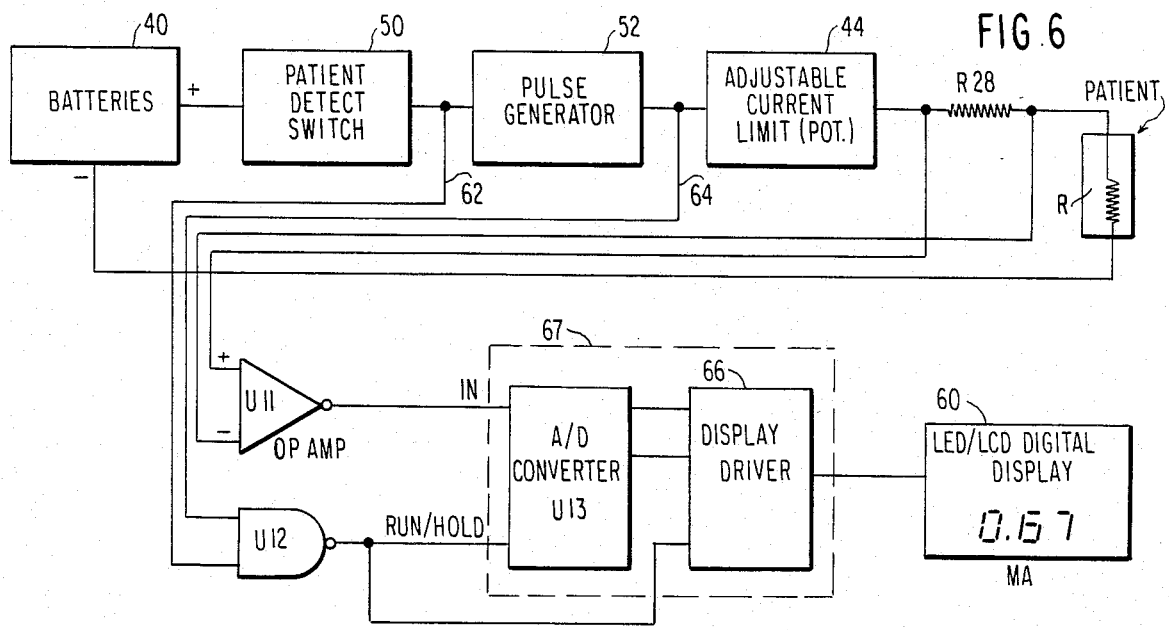
FIG. 6 is a block and schematic diagram of the electronics for the embodiment illustrated in FIGS. 5A and 5B.

FIG. 5A, 5B and 6 illustrate another embodiment of the invention wherein an LED or LCD digital display 60 is also mounted in the top surface of the nerve stimulator/locator unit 10 for the purpose of visually displaying to the operating physician the actual value of each current pulse (0.3 to 3 milliamps) that is flowing through the patient's body. A low value (1K) resistor R28 is connected in series with the current flowing from the potentiometer and into the needle 16. (In this case, resistor R7 has a value of only 2.3K). The voltage dropped across this resistor R28 is thus proportional to the current actually flowing through the patient's body. This voltage is applied to an operational amplifier U11 which amplifies the voltage and applies it to an analog-to-digital converter U13. The outputs of the patient detect switch 50 and the pulse generator 52 are also applied to a logic gate U12 whose output is also applied to the converter U13, thereby causing the converter effectively to sample the current only during the pulse periods. The outputs of the converter U13 and the logic gate U12 are applied to a display driver 66 whose output drives the digital display 60. Driver 66 contains appropriate latches and decoders to drive a display 60 containing 4 digits and 7 segments per digit. In practice, converter U13 and driver 66 are formed on a single integrated circuit ship 67, such as an INTERSIL ICL 7116 for fan LCD display or ICL 7117 for an LED display; such a chip is termed a "3½ Digit Single Chip A/D Converter with Display Hold." Thus, the display is enabled only when the patient detect switch has detected the insertion of the needle into the patient's body. The displayed valve will be updated after each pulse and will continue to display each pulse value until the next pulse is applied to the patient's body.

We claim:

1. A nerve stimulator/locator unit for applying current pulses to a patient's body through an injection needle connected to a syringe, said unit comprising:
    a housing;
    pulse generator means mounted in said housing for generating a series of output current pulses;
    indicator means mounted on said housing for producing a visual indication of the generation of each pulse;
    manually controlled current-adjusting means mounted in said housing for adjusting the current values of the pulses;
    connector means for electrically connecting the output of said pulse generator means to an injection needle; and
    clamping means, fixed to said housing, for clamping said housing directly to a syringe.

2. A unit as defined in claim 1 further comprising patient detector means mounted in said housing for inhibiting the generation of the pulses except when the injecting needle is in contact with the patient's body.

3. A unit as defined in claim 2 further comprising display means, mounted on said housing and electrically coupled to the output of said current-adjusting means, for displaying the values of the current pulses applied to the patient's body.

4. A unit as defined in claim 2 further comprising a power supply mounted in said housing; and wherein said detector means comprises:
    a normally non-conducting transistor switch connected between said power supply and said pulse generator means; and
    current-sensing means, coupled between said power supply and said connector means, for rendering said transistor switch conducting when a minute current flows through said sensing means upon contact being made between the injection needle and the patient's body.

5. In combination:
    a syringe coupled to an injection needle, and
    a self-contained nerve stimulator/locating unit clamped to said syringe;
    said unit comprising:
    a housing,
    pulse generator means mounted in said housing for generating a series of output current pulses;
    indicator means mounted on said housing for producing a visual indication of the generation of each pulse;
    manually controlled current-adjusting means mounted in said housing for adjusting the current values of the pulses; and
    connector means for electrically connecting the output of said pulse generator means to said injection needle.

6. A combination as defined in claim 5 further comprising patient detector means mounted in said housing for inhibiting the generation of the pulses except when said injection needle is in contact with the patient's body.

7. A combination as defined in claim 6 further comprising display means, mounted on said housing and electrically coupled to the output of said current-adjusting means, for displaying the value of the current pulses applied to the patient's body.

8. A combination as defined in claim 6 wherein said unit comprises:
    a power supply in said housing; and
    wherein said patient detector means comprises a normally non-conducting transistor switch connected between said power supply and said pulse generating means, and current-sensing means, coupled between said power supply and said connecting means, for rendering said transistor switch conducting when a minute current flows through said current-sensing means upon contact being made between said injection needle and the patient's body.

9. A combination as defined in claim 5 wherein all but the tip of said needle is coated with an electrically insulated material, and
    wherein said connector means comprises an electrical connector integral with said needle.

* * * * *